(12) United States Patent
Soppet et al.

(10) Patent No.: US 6,884,594 B2
(45) Date of Patent: Apr. 26, 2005

(54) ANTIBODIES TO GROWTH FACTOR HTTER36

(75) Inventors: Daniel R. Soppet, Centreville, VA (US); Haodong Li, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 275 days.

(21) Appl. No.: 10/117,178

(22) Filed: Apr. 8, 2002

(65) Prior Publication Data

US 2002/0137143 A1 Sep. 26, 2002

Related U.S. Application Data

(62) Division of application No. 09/357,905, filed on Jul. 21, 1999, now Pat. No. 6,413,933, which is a division of application No. 08/827,336, filed on Mar. 26, 1997, now Pat. No. 6,004,780.
(60) Provisional application No. 60/014,098, filed on Mar. 26, 1996.

(51) Int. Cl.$^7$ .......................... C07K 16/22; C12N 5/12; G01N 33/53
(52) U.S. Cl. .................. 435/7.1; 435/335; 436/501; 530/387.1; 530/387.3; 530/387.7; 530/387.9; 530/388.1; 530/388.15
(58) Field of Search .......................... 436/501; 435/335, 435/7.1; 530/387.1, 387.3, 387.7, 387.9, 388.1, 388.15

(56) References Cited

U.S. PATENT DOCUMENTS 5,808,007 A 9/1998 Lee et al.

FOREIGN PATENT DOCUMENTS

| WO | WO 94/15949 A1 | 7/1994 |
| WO | WO 94/15965 A1 | 7/1994 |
| WO | WO 95/10539 A1 | 4/1995 |
| WO | WO 98/41634 A1 | 9/1998 |

OTHER PUBLICATIONS

PIR Accession No. A46607 (Jul., 2004).
Bowie et al., Deciphering the Message in Protein Sequences: Tolerance to Amino Acid Substitutions, *Science*, 247:1306–1310 (1990).
George et al., Current Methods in Sequence Comparison and Analysis, in Macromolecular Sequencing and Synthesis, 1988, pp. 127–149, Alan R. Liss, Inc.
McPherron et al., GDF–3 and GDF–9: Two New Members of the Transforming Growth Factor–β Superfamily Containing a Novel Pattern of Cysteines, *Journal of Biol. Chem.*, Feb. 15, 1993, pp. 3444–3449, 268(5), USA.
Ngo et al., Computational Cmplexity Protein Structure Prediction and the Levinthal Paradox, *The Protein Folding Problem and Teriary Structure Prediction*. Bikhauser, Boston, pp. 492–495 (1994).
Robson et al., Introduction of Proteins Engineering, *Elsevier*, New York p. 41 (1986).
Saharinen et al., Identification and Characterization of a New Latent Transforming Growth Factor–β–binding Protein, *Journal Biol. Chem.*, Jul. 17, 1998, pp. 18459–18469, 273(29), USA.
Wells et al., Additivity of Mutational effects in Proteins, *Biochemistry*, 29(37):8509–8517 (1990).

*Primary Examiner*—Christine J. Saoud
(74) *Attorney, Agent, or Firm*—Human Genome Sciences, Inc.

(57) ABSTRACT

The present invention discloses Growth Factor HTTER36 polypeptides and polynucleotides encoding such polypeptides. Also disclosed are antibodies and fragments thereof that specifically bind to such polypeptides. Also provided is a procedure for producing such polypeptides by recombinant techniques and therapeutic uses of the polypeptides which include stimulating cellular growth and differentiation, bone formation and wound healing. Also disclosed are antagonists against such polypeptide and their use as a therapeutic to treat neoplasia and to prevent the formation of extracellular matrix molecules in the liver and lung. Also disclosed are diagnostic assays for detecting altered levels of the polypeptide of the present invention and mutations in the nucleic acid sequences which encode the polypeptides of the invention.

71 Claims, 4 Drawing Sheets

The Sequence for HTTER36

```
              10                  30                  50
 -39  AATTCGGCACGAGCCCGGTCTGACAGCCACTCCAGAGGCCATGCTTCGTTTCTTGCCAGA    20
                                                M  L  R  F  L  P  D     7

70                  90                 110
  21  TTTGGCTTTCAGCTTCCTGTTAATTCTGGCTTTGGGCCAGGCAGTCCAATTTCAAGAATA    80
   8   L  A  F  S  F  L  L  I  L  A  L  G  Q  A  V  Q  F  Q  E  Y     27

130                 150                 170
  81  TGTCTTTCTCCAATTTCTGGGCTTAGATAAGGCGCCTTCACCCCAGAAGTTCCAACCTGT   140
  28   V  F  L  Q  F  L  G  L  D  K  A  P  S  P  Q  K  F  Q  P  V     47

190                 210                 230
 141  GCCTTATATCTTGAAGAAAATTTTCCAGGATCGCGAGGCAGCAGCGACCACTGGGGTCTC   200
  48   P  Y  I  L  K  K  I  F  Q  D  R  E  A  A  A  T  T  G  V  S     67

250                 270                 290
 201  CCGAGACTTATGCTACGTAAAGGAGCTGGGCGTCCGCGGGAATGTACTTCGCTTTCTCCC   260
  68   R  D  L  C  Y  V  K  E  L  G  V  R  G  N  V  L  R  F  L  P     87

310                 330                 350
 261  AGACCAAGGTTTCTTTCTTTACCCAAAGAAAATTTCCCAAGCTTCCTCCTGCCTGCAGAA   320
  88   D  Q  G  F  F  L  Y  P  K  K  I  S  Q  A  S  S  C  L  Q  K    107

370                 390                 410
 321  GCTCCTCTACTTTAACCTGTCTGCCATCAAAGAAAGGGAACAGTTGACATTGGCCCAGCT   380
 108   L  L  Y  F  N  L  S  A  I  K  E  R  E  Q  L  T  A  Q  L       127

430                 450                 470
 381  GGGCCTGGACTTGGGGCCCAATTCTTACTATAACCTGGGACCAGAGCTGGAACTGGCTCT   440
 128   G  L  D  L  G  P  N  S  Y  Y  N  L  G  P  E  L  E  L  A  L    147

490                 510                 530
 441  GTTCCTGGTTCAGGAGCCTCATGTGTGGGGCCAGACCACCCCTAAGCCAGGTAAAATGTT   500
 148   F  L  V  Q  E  P  H  V  W  G  Q  T  T  P  K  P  G  K  M  F    167

550                 570                 590
 501  TGTGTTGCGGTCAGTCCCATGGCCACAAGGTGCTGTTCACTTCAACCTGCTGGATGTAGC   560
 168   V  L  R  S  V  P  W  P  Q  G  A  V  H  F  N  L  L  D  V  A    187

610                 630                 650
 561  TAAGGATTGGAATGACAACCCCCGGAAAAATTTCGGGTTATTCCTGGAGATACTGGTCAA   620
 188   K  D  W  N  D  N  P  R  K  N  F  G  L  F  L  E  I  L  V  K    207

670                 690                 710
 621  AGAAGATAGAGACTCAGGGGTGAATTTTCAGCCTGAAGACACCTGTGCCAGACTAAGATG   680
 208   E  D  R  D  S  G  V  N  F  Q  P  E  D  T  C  A  R  L  R  C    227
```

FIG. 1A

```
          730                 750                 770
 681 CTCCCTTCATGCTTCCCTGCTGGTGGTGACTCTCAACCCTGATCAGTGCCACCCTTCTCG  740
 228   S   L   H   A   S   L   L   V   V   T   L   N   P   D   Q   C   H   P   S   R   247

790                 810                 830
 741 GAAAAGGAGAGCAGCCATCCCTGTCCCCAAGCTTTCTTGTAAGAACCTCTGCCACCGTCA  800
 248   K   R   R   A   A   I   P   V   P   K   L   S   C   K   N   L   C   H   R   H   267

850                 870                 890
 801 CCAGCTATTCATTAACTTCCGGGACCTGGGTTGGCACAAGTGGATCATTGCCCCCAAGGG  860
 268   Q   L   F   I   N   F   R   D   L   G   W   H   K   W   I   I   A   P   K   G   287

910                 930                 950
 861 GTTCATGGCAAATTACTGCCATGGAGAGTGTCCCTTCTCACTGACCATCTCTCTCAACAG  920
 288   F   M   A   N   Y   C   H   G   E   C   P   F   S   L   T   I   S   L   N   R   307

970                 990                1010
 921 GTCCAATTATGCTTTCATGCAAGCCCTGATGCATGCCGTTGACCCAGAGATCCCCCAGGC  980
 308   S   N   Y   A   F   M   Q   A   L   M   H   A   V   D   P   E   I   P   Q   A   327

1030                1050                1070
 981 TGTGTGTATCCCCACCAAGCTGTCTCCCATTTCCATGCTCTACCAGGACAATAATGACAA 1040
 328   V   C   I   P   T   K   L   S   P   I   S   M   L   Y   Q   D   N   N   D   N   347

1090                1110                1130
1041 TGTCATTCTACGACATTATGAAGACATGGTAGTCGATGAATGTGGGTGTGGGTAGGATGT 1100
 348   V   I   L   R   H   Y   E   D   M   V   V   D   E   C   G   C   G   *           364

1150                1170                1190
1101 CAGAAATGGGAATAGAAGGAGTGTTCTTAGGGTAAACTTTTAATAAAACTACCTAGCTGG 1160

1210
1161 TTTATGCCCAAA                                                    1172
```

FIG. 1B

```
  1 MLRFLPDLAFSFLLI.LALGQAVQFQEYVFLQFLGLDKAPSPQKFQPVPY  49
    | .: . ||::||| : |::||. :||: :||||||:|||||::|||||
  1 MQPYQRLLALGFLLLTLPWGQTSEFQDSDLLQFLGLEKAPSPHRFQPVPR  50

50 ILKKIFQDREAAATTGVSRDLCYVKELGVRGNVLRFLPDQGFFLYPKKIS  99
    :|:||:..||||| ..|.|.||||||||||||||:|.:||||||| ..|
 51 VLRKIIRAREAAAASGASQDLCYVKELGVRGNLLQLLPDQGFFLNTQKPF 100

100 QASSCLQKLLYFNLSAIKEREQLTLAQLGLDLGPNSYYNLGPELELALFL 149
    |.:|||||:|||||||||||:..||:|||.|||||.||||| ||| :|| :
101 QDGSCLQKVLYFNLSAIKEKAKLTMAQLTLDLGPRSYYNLRPELVVALSV 150

150 VQEPHVWGQTTPKPGKMFVLRSVPWPQGAVHFNLLDVAKDWNDNPRKNFG 199
    ||:. |||.. ||.|:::.||||| |||.::||| :. |||..|. ||::
151 VQDRGVWGRSHPKVGRLLFLRSVPGPQGQLQFNLQGALKDWSSNRLKNLD 200

200 LFLEILVKEDRDSGVNFQPEDTCARLRCSLHASLLVVTLNPDQCHP.SRK 248
    | ||||||||| | |..|||:.|..| |||||||||||||.:||| |||
201 LHLEILVKEDRYSRVTVQPENPCDPLLRSLHASLLVVTLNPKHCHPSSRK 250

249 RRAAIPVPKLSCKNLCHRHQLFINFRDLGWHKWIIAPKGFMANYCHGECP 298
    |||||.||| |:|:||||||||||.||||||:|||||||||||||||||
251 RRAAISVPKGFCRNFCHRHQLFINFQDLGWHKWVIAPKGFMANYCHGECP 300

299 FSLTISLNRSNYAFMQALMHAVDPEIPQAVCIPTKLSPISMLYQDNNDNV 348
    ||:|. ||.|||||||||||.||.:|.|||:|||||||||||||.:.||
301 FSMTTYLNSSNYAFMQALMHMADPKVPKAVCVPTKLSPISMLYQDSDKNV 350

349 ILRHYEDMVVDECGCG 364
    ||||||||||||||||
351 ILRHYEDMVVDECGCG 366
```

FIG. 2

Effect of GDF-3 (HG11000-E1) on IFN gamma Production by Th0, TH1 and Th2 cells Controls:
IL-12 (5ng/mL)
    Th0: 13.96 ± .1 (SD)
    Th1: 16.33 ± .1 (SD)
    Th2: 50.79 ± .1 (SD)
IL-4 (5ng/mL)
    Th0:   .39  ± .1 (SD)
    Th1: 58.7   ± .1 (SD)
    Th2:   .631 ± .1 (SD)

SEQUENCE LISTING

<160> NUMBER OF SEQ ID NOS: 9

<210> SEQ ID NO 1
<211> LENGTH: 1212
<212> TYPE: DNA
<213> ORGANISM: Homo sapiens
<220> FEATURE:
<221> NAME/KEY: CDS
<222> LOCATION: (41)..(1132)
<223> OTHER INFORMATION:

<400> SEQUENCE: 1

```
aattcggcac gagcccggtc tgacagccac tccagaggcc atg ctt cgt ttc ttg         55
                                           Met Leu Arg Phe Leu
                                           1               5 cca gat ttg gct ttc agc ttc ctg tta att ctg gct ttg ggc cag gca        103
Pro Asp Leu Ala Phe Ser Phe Leu Leu Ile Leu Ala Leu Gly Gln Ala
            10                  15                  20 gtc caa ttt caa gaa tat gtc ttt ctc caa ttt ctg ggc tta gat aag        151
Val Gln Phe Gln Glu Tyr Val Phe Leu Gln Phe Leu Gly Leu Asp Lys
        25                  30                  35 gcg cct tca ccc cag aag ttc caa cct gtg cct tat atc ttg aag aaa        199
Ala Pro Ser Pro Gln Lys Phe Gln Pro Val Pro Tyr Ile Leu Lys Lys
    40                  45                  50 att ttc cag gat cgc gag gca gca gcg acc act ggg gtc tcc cga gac        247
Ile Phe Gln Asp Arg Glu Ala Ala Ala Thr Thr Gly Val Ser Arg Asp
55                  60                  65 tta tgc tac gta aag gag ctg ggc gtc cgc ggg aat gta ctt cgc ttt        295
Leu Cys Tyr Val Lys Glu Leu Gly Val Arg Gly Asn Val Leu Arg Phe
70                  75                  80                  85 ctc cca gac caa ggt ttc ttt ctt tac cca aag aaa att tcc caa gct        343
Leu Pro Asp Gln Gly Phe Phe Leu Tyr Pro Lys Lys Ile Ser Gln Ala
                90                  95                  100 tcc tcc tgc ctg cag aag ctc ctc tac ttt aac ctg tct gcc atc aaa        391
Ser Ser Cys Leu Gln Lys Leu Leu Tyr Phe Asn Leu Ser Ala Ile Lys
            105                 110                 115 gaa agg gaa cag ttg aca ttg gcc cag ctg ggc ctg gac ttg ggg ccc        439
Glu Arg Glu Gln Leu Thr Leu Ala Gln Leu Gly Leu Asp Leu Gly Pro
        120                 125                 130 aat tct tac tat aac ctg gga cca gag ctg gaa ctg gct ctg ttc ctg        487
Asn Ser Tyr Tyr Asn Leu Gly Pro Glu Leu Glu Leu Ala Leu Phe Leu
    135                 140                 145 gtt cag gag cct cat gtg tgg ggc cag acc acc cct aag cca ggt aaa        535
Val Gln Glu Pro His Val Trp Gly Gln Thr Thr Pro Lys Pro Gly Lys
150                 155                 160                 165 atg ttt gtg ttg cgg tca gtc cca tgg cca caa ggt gct gtt cac ttc        583
Met Phe Val Leu Arg Ser Val Pro Trp Pro Gln Gly Ala Val His Phe
                170                 175                 180 aac ctg ctg gat gta gct aag gat tgg aat gac aac ccc cgg aaa aat        631
Asn Leu Leu Asp Val Ala Lys Asp Trp Asn Asp Asn Pro Arg Lys Asn
            185                 190                 195 ttc ggg tta ttc ctg gag ata ctg gtc aaa gaa gat aga gac tca ggg        679
Phe Gly Leu Phe Leu Glu Ile Leu Val Lys Glu Asp Arg Asp Ser Gly
        200                 205                 210 gtg aat ttt cag cct gaa gac acc tgt gcc aga cta aga tgc tcc ctt        727
Val Asn Phe Gln Pro Glu Asp Thr Cys Ala Arg Leu Arg Cys Ser Leu
    215                 220                 225
```

-continued

| | | |
|---|---|---|
| cat gct tcc ctg ctg gtg gtg act ctc aac cct gat cag tgc cac cct<br>His Ala Ser Leu Leu Val Val Thr Leu Asn Pro Asp Gln Cys His Pro<br>230                                235                        240                       245 | 775 | |

```
cat gct tcc ctg ctg gtg gtg act ctc aac cct gat cag tgc cac cct        775
His Ala Ser Leu Leu Val Val Thr Leu Asn Pro Asp Gln Cys His Pro
230                 235                 240                 245 tct cgg aaa agg aga gca gcc atc cct gtc ccc aag ctt tct tgt aag        823
Ser Arg Lys Arg Arg Ala Ala Ile Pro Val Pro Lys Leu Ser Cys Lys
            250                 255                 260 aac ctc tgc cac cgt cac cag cta ttc att aac ttc cgg gac ctg ggt        871
Asn Leu Cys His Arg His Gln Leu Phe Ile Asn Phe Arg Asp Leu Gly
        265                 270                 275 tgg cac aag tgg atc att gcc ccc aag ggg ttc atg gca aat tac tgc        919
Trp His Lys Trp Ile Ile Ala Pro Lys Gly Phe Met Ala Asn Tyr Cys
    280                 285                 290 cat gga gag tgt ccc ttc tca ctg acc atc tct ctc aac agg tcc aat        967
His Gly Glu Cys Pro Phe Ser Leu Thr Ile Ser Leu Asn Arg Ser Asn
295                 300                 305 tat gct ttc atg caa gcc ctg atg cat gcc gtt gac cca gag atc ccc       1015
Tyr Ala Phe Met Gln Ala Leu Met His Ala Val Asp Pro Glu Ile Pro
310                 315                 320                 325 cag gct gtg tgt atc ccc acc aag ctg tct ccc att tcc atg ctc tac       1063
Gln Ala Val Cys Ile Pro Thr Lys Leu Ser Pro Ile Ser Met Leu Tyr
                330                 335                 340 cag gac aat aat gac aat gtc att cta cga cat tat gaa gac atg gta       1111
Gln Asp Asn Asn Asp Asn Val Ile Leu Arg His Tyr Glu Asp Met Val
            345                 350                 355 gtc gat gaa tgt ggg tgt ggg taggatgtca gaaatgggaa tagaaggagt          1162
Val Asp Glu Cys Gly Cys Gly
        360 gttcttaggg taaactttta ataaaactac ctagctggtt tatgcccaaa                 1212
```

<210> SEQ ID NO 2
<211> LENGTH: 364
<212> TYPE: PRT
<213> ORGANISM: Homo sapiens

<400> SEQUENCE: 2

```
Met Leu Arg Phe Leu Pro Asp Leu Ala Phe Ser Phe Leu Leu Ile Leu
1               5                   10                  15

Ala Leu Gly Gln Ala Val Gln Phe Gln Glu Tyr Val Phe Leu Gln Phe
            20                  25                  30

Leu Gly Leu Asp Lys Ala Pro Ser Pro Gln Lys Phe Gln Pro Val Pro
        35                  40                  45

Tyr Ile Leu Lys Lys Ile Phe Gln Asp Arg Glu Ala Ala Ala Thr Thr
    50                  55                  60

Gly Val Ser Arg Asp Leu Cys Tyr Val Lys Glu Leu Gly Val Arg Gly
65                  70                  75                  80

Asn Val Leu Arg Phe Leu Pro Asp Gln Gly Phe Phe Leu Tyr Pro Lys
                85                  90                  95

Lys Ile Ser Gln Ala Ser Ser Cys Leu Gln Lys Leu Leu Tyr Phe Asn
            100                 105                 110

Leu Ser Ala Ile Lys Glu Arg Glu Gln Leu Thr Leu Ala Gln Leu Gly
        115                 120                 125

Leu Asp Leu Gly Pro Asn Ser Tyr Tyr Asn Leu Gly Pro Glu Leu Glu
    130                 135                 140

Leu Ala Leu Phe Leu Val Gln Glu Pro His Val Trp Gly Gln Thr Thr
145                 150                 155                 160
```

-continued

```
Pro Lys Pro Gly Lys Met Phe Val Leu Arg Ser Val Pro Trp Pro Gln
                165                 170                 175
Gly Ala Val His Phe Asn Leu Leu Asp Val Ala Lys Asp Trp Asn Asp
            180                 185                 190
Asn Pro Arg Lys Asn Phe Gly Leu Phe Leu Glu Ile Leu Val Lys Glu
        195                 200                 205
Asp Arg Asp Ser Gly Val Asn Phe Gln Pro Glu Asp Thr Cys Ala Arg
    210                 215                 220
Leu Arg Cys Ser Leu His Ala Ser Leu Leu Val Val Thr Leu Asn Pro
225                 230                 235                 240
Asp Gln Cys His Pro Ser Arg Lys Arg Arg Ala Ala Ile Pro Val Pro
                245                 250                 255
Lys Leu Ser Cys Lys Asn Leu Cys His Arg His Gln Leu Phe Ile Asn
                260                 265                 270
Phe Arg Asp Leu Gly Trp His Lys Trp Ile Ile Ala Pro Lys Gly Phe
            275                 280                 285
Met Ala Asn Tyr Cys His Gly Glu Cys Pro Phe Ser Leu Thr Ile Ser
290                 295                 300
Leu Asn Arg Ser Asn Tyr Ala Phe Met Gln Ala Leu Met His Ala Val
305                 310                 315                 320
Asp Pro Glu Ile Pro Gln Ala Val Cys Ile Pro Thr Lys Leu Ser Pro
                325                 330                 335
Ile Ser Met Leu Tyr Gln Asp Asn Asn Asp Asn Val Ile Leu Arg His
                340                 345                 350
Tyr Glu Asp Met Val Val Asp Glu Cys Gly Cys Gly
            355                 360

<210> SEQ ID NO 3
<211> LENGTH: 40
<212> TYPE: DNA
<213> ORGANISM: Artificial sequence
<220> FEATURE:
<223> OTHER INFORMATION: 5' primer with a BamHI site and 18 nt of
      HTTER36 coding sequence.

<400> SEQUENCE: 3
gaaaggatcc gcagccatcc ctgtccccaa actttcttgt                             40

<210> SEQ ID NO 4
<211> LENGTH: 40
<212> TYPE: DNA
<213> ORGANISM: Artificial sequence
<220> FEATURE:
<223> OTHER INFORMATION: 3' primer with a HindIII site, a stop codon and
      15 nt of HTTER36 sequence.

<400> SEQUENCE: 4
tccttctatt caagcttctg acatcctacc cacacccaca                             40

<210> SEQ ID NO 5
<211> LENGTH: 35
<212> TYPE: DNA
<213> ORGANISM: Artificial sequence
<220> FEATURE:
<223> OTHER INFORMATION: 5' primer with a BamHI site, start codon, and
      17 nt of HTTER36 coding sequence.

<400> SEQUENCE: 5
cagggatccg ccatcatgct tcgtttcttg ccaga                                  35
```

<210> SEQ ID NO 6
<211> LENGTH: 33
<212> TYPE: DNA
<213> ORGANISM: Artificial sequence
<220> FEATURE:
<223> OTHER INFORMATION: 3' primer with an Asp718 site and 23 nt of
     HTTER36 3' sequence.

<400> SEQUENCE: 6
cttcggtacc catttctgac atcctaccca cac                                    33

<210> SEQ ID NO 7
<211> LENGTH: 36
<212> TYPE: DNA
<213> ORGANISM: Artificial sequence
<220> FEATURE:
<223> OTHER INFORMATION: 5' primer with a BamHI site followed by an
     efficient signal for translation, and 18 nt of the gene.

<400> SEQUENCE: 7
acagcggatc cagccaccat gcttcgtttc ttgcca                                 36

<210> SEQ ID NO 8
<211> LENGTH: 40
<212> TYPE: DNA
<213> ORGANISM: Artificial sequence
<220> FEATURE:
<223> OTHER INFORMATION: 3' primer with a BamHI site and 29 nt of 3'
     gene sequence.

<400> SEQUENCE: 8
tccttcggat cccatttctg acatcctacc cacacccaca                             40

<210> SEQ ID NO 9
<211> LENGTH: 366
<212> TYPE: PRT
<213> ORGANISM: Mus musculus

<400> SEQUENCE: 9

Met Gln Pro Tyr Gln Arg Leu Leu Ala Leu Gly Phe Leu Leu Leu Thr
1               5                   10                  15

Leu Pro Trp Gly Gln Thr Ser Glu Phe Gln Asp Ser Asp Leu Leu Gln
            20                  25                  30

Phe Leu Gly Leu Glu Lys Ala Pro Ser Pro His Arg Phe Gln Pro Val
        35                  40                  45

Pro Arg Val Leu Arg Lys Ile Ile Arg Ala Arg Glu Ala Ala Ala Ala
    50                  55                  60

Ser Gly Ala Ser Gln Asp Leu Cys Tyr Val Lys Glu Leu Gly Val Arg
65                  70                  75                  80

Gly Asn Leu Leu Gln Leu Leu Pro Asp Gln Gly Phe Phe Leu Asn Thr
                85                  90                  95

Gln Lys Pro Phe Gln Asp Gly Ser Cys Leu Gln Lys Val Leu Tyr Phe
            100                 105                 110

Asn Leu Ser Ala Ile Lys Glu Lys Ala Lys Leu Thr Met Ala Gln Leu
        115                 120                 125

Thr Leu Asp Leu Gly Pro Arg Ser Tyr Tyr Asn Leu Arg Pro Glu Leu
    130                 135                 140

Val Val Ala Leu Ser Val Val Gln Asp Arg Gly Val Trp Gly Arg Ser
145                 150                 155                 160

His Pro Lys Val Gly Arg Leu Leu Phe Leu Arg Ser Val Pro Gly Pro
                165                 170                 175

```
Gln Gly Gln Leu Gln Phe Asn Leu Gln Gly Ala Leu Lys Asp Trp Ser
            180             185             190

Ser Asn Arg Leu Lys Asn Leu Asp Leu His Leu Glu Ile Leu Val Lys
        195             200             205

Glu Asp Arg Tyr Ser Arg Val Thr Val Gln Pro Glu Asn Pro Cys Asp
    210             215             220

Pro Leu Leu Arg Ser Leu His Ala Ser Leu Leu Val Val Thr Leu Asn
225             230             235             240

Pro Lys His Cys His Pro Ser Ser Arg Lys Arg Arg Ala Ala Ile Ser
            245             250             255

Val Pro Lys Gly Phe Cys Arg Asn Phe Cys His Arg His Gln Leu Phe
            260             265             270

Ile Asn Phe Gln Asp Leu Gly Trp His Lys Trp Val Ile Ala Pro Lys
        275             280             285

Gly Phe Met Ala Asn Tyr Cys His Gly Glu Cys Pro Phe Ser Met Thr
    290             295             300

Thr Tyr Leu Asn Ser Ser Asn Tyr Ala Phe Met Gln Ala Leu Met His
305             310             315             320

Met Ala Asp Pro Lys Val Pro Lys Ala Val Cys Val Pro Thr Lys Leu
            325             330             335

Ser Pro Ile Ser Met Leu Tyr Gln Asp Ser Asp Lys Asn Val Ile Leu
            340             345             350

Arg His Tyr Glu Asp Met Val Val Asp Glu Cys Gly Cys Gly
            355             360             365
```

ANTIBODIES TO GROWTH FACTOR HTTER36

CROSS REFERENCE TO RELATED APPLICATIONS

This application is a Divisional of U.S. patent application Ser. No. 09/357,905, filed Jul. 21, 1999 (now U.S. Pat. No. 6,413,933); which is a Divisional of U.S. patent application Ser. No. 08/827,336, filed Mar. 26, 1997 (now U.S. Pat. No. 6,004,780); which claims the benefit under 35 U.S.C. § 119(e) of to U.S. Provisional Patent Application Ser. No. 60/014,098, filed Mar. 26, 1996; all of which are hereby incorporated by reference in their entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a human transforming growth factor. More particularly, the polypeptide of the present invention has been putatively identified as a member of the transforming growth factor Beta super-family and is sometimes hereafter referred to as "HTTER36". The invention also relates to inhibiting the action of such polypeptides.

This invention relates to a polynucleotide and polypeptide molecules which are structurally and functionally related to TGF-β. The transforming growth factor-beta family of peptide growth factors includes five members, termed TGF-β1 through TGF-β5, all of which form homo-dimers of approximately 25 kd. The TGF-β family belongs to a larger, extended super family of peptide signaling molecules that includes the Muellerian inhibiting substance (Cate, R. L. et al., Cell, 45:685–698 (1986)), decapentaplegic (Padgett, R. W. et al., Nature, 325:81–84 (1987)), bone morphogenic factors (Wozney, J. M. et al., Science, 242:1528–1534 (1988)), vg1 (Weeks, D. L., and Melton, D. A., Cell, 51:861–867 (1987)), activins (Vale, W. et al., Nature, 321:776–779 (1986)), and inhibins (Mason, A. J. et al., Nature, 318:659–663 (1985)). These factors are similar to TGF-β in overall structure, but share only approximately 25% amino acid identity with the TGF-β proteins and with each other. All of these molecules are thought to play important roles in modulating growth, development and differentiation. The protein of the present invention, PGF, retains the seven cysteine residues conserved in the C-terminal, active domain of TGF-β.

TGF-β was originally described as a factor that induced normal rat kidney fibroblasts to proliferate in soft agar in the presence of epidermal growth factor (Roberts, A. B. et al., PNAS USA, 78:5339–5343 (1981)). TGF-β has subsequently been shown to exert a number of different effects in a variety of cells. For example, TGF-β can inhibit the differentiation of certain cells of mesodermal origin (Florini, J. R. et al., J. Biol. Chem., 261:1659–16513 (1986)), induced the differentiation of others (Seyedine, S. M. et al., PNAS USA, 82:2267–2271 (1985)), and potently inhibit proliferation of various types of epithelial cells, (Tucker, R. F., Science, 226:705–707 (1984)). This last activity has lead to the speculation that one important physiologic role for TGF-β is to maintain the repressed growth state of many types of cells. Accordingly, cells that lose the ability to respond to TGF-β are more likely to exhibit uncontrolled growth and to become tumorigenic. Indeed, certain tumors such as retinoblastomas lack detectable TGF-β receptors at their cell surface and fail to respond to TGF-β, while their normal counterparts express self-surface receptors in their growth are potently inhibited by TGF-β (Kim Chi, A. et al., Science, 240:196–198 (1988)).

More specifically, TGF-β1 stimulates the anchorage-independent growth of normal rat kidney fibroblasts (Robert et al., PNAS USA, 78:5339–5343 (1981)). Since then it has been shown to be a multi-functional regulator of cell growth and differentiation (Sporn et al., Science, 233:532–534 (1986)) being capable of such diverse effects of inhibiting the growth of several human cancer cell lines (Roberts et al., PNAS-USA, 82:119–123 (1985)), mouse keratinocytes, (Coffey et al., Cancer RES., 48:1596–1602 (1988)), and T and B lymphocytes (Kehrl et al., J.Exp.Med., 163:1037–1050 (1986)). It also inhibits early hematopoietic progenitor cell proliferation (Goey et al., J.Immunol., 143:877–880 (1989)), stimulates the induction of differentiation of rat muscle mesenchymal cells and subsequent production of cartilage-specific macro molecules (Seyedine et al., J. Biol. Chem., 262:1946–1949 (1986)), causes increased synthesis and secretion of collagen (Ignotz et al., J. Biol. Chem., 261:4337–4345 (1986)), stimulates bone formation (Noda et al., Endocrinology, 124:2991–2995 (1989)), and accelerates the healing of incision wounds (Mustoe et al., Science, 237:1333–1335 (1987)).

Further, TGF-β1 stimulates formation of extracellular matrix molecules in the liver and lung. When levels of TGF-β1 are higher than normal, formation of fiber occurs in the extracellular matrix of the liver and lung, which can be fatal. High levels of TGF-β1 occur due to chemotherapy and bone marrow transplant as an attempt to treat cancers, e.g. breast cancer.

A second protein termed TGF-β2 was isolated from several sources including demineralized bone, a human prostatic adenocarcinoma cell line (Ikeda et al., Bio.Chem., 26:2406–2410 (1987)). TGF-β2 shared several functional similarities with TGF-β1. These proteins are now known to be members of a family of related growth modulatory proteins including TGF-β3 (Ten-Dijke et al., PNAS, USA, 85:471–4719 (1988)), Muellerian inhibitory substance and the inhibins. The polypeptide of the present invention has been putatively identified as a member of this family of related growth modulatory proteins.

In accordance with one aspect of the present invention, there are provided novel mature polypeptides, as well as biologically active and diagnostically or therapeutically useful fragments, analogs and derivatives thereof. The polypeptides of the present invention are of human origin.

In accordance with another aspect of the present invention, there are provided isolated nucleic acid molecules encoding the polypeptides of the present invention, including mRNAs, cDNAs, genomic DNAs as well as analogs and biologically active and diagnostically or therapeutically useful fragments thereof.

In accordance with another aspect of the present invention there is provided an isolated nucleic acid molecule encoding a mature polypeptide expressed by the human cDNA contained in ATCC Deposit No. 97349.

In accordance with yet a further aspect of the present invention, there are provided processes for producing such polypeptide by recombinant techniques comprising culturing recombinant prokaryotic and/or eukaryotic host cells, containing a nucleic acid sequence encoding a polypeptide of the present invention.

In accordance with yet a further aspect of the present invention, there are provided processes for utilizing such polypeptides, or polynucleotides encoding such polypeptides for therapeutic purposes, for example, to stimulate cellular growth and differentiation, stimulate bone formation and wound healing.

In accordance with yet a further aspect of the present invention, there is also provided nucleic acid probes comprising nucleic acid molecules of sufficient length to specifically hybridize to nucleic acid sequences of the present invention.

In accordance with yet a further aspect of the present invention, there are provided antibodies against such polypeptides.

In accordance with yet a further aspect of the present invention, there are provided agonists to the polypeptide of the present invention.

In accordance with yet another aspect of the present invention, there are provided antagonists to such polypeptides, which may be used to inhibit the action of such polypeptides, for example, in the treatment of, neoplasia of cells whose growth are stimulated by the polypeptide of the present invention and preventing formation of extracellular matrix molecules in the liver and lung.

In accordance with still another aspect of the present invention, there are provided diagnostic assays for detecting diseases related to over expression of the polypeptide of the present invention and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–B depicts the cDNA sequence and corresponding deduced amino acid sequence of HTTER36. The standard one-letter abbreviations for amino acids are used. The putative signal sequence has been underlined.

FIG. 2 is an illustration of comparative amino acid sequence homology between HTTER36 (top line) and *Mus musculus* putative transforming growth factor-beta, "GDF-3" (SEQ ID NO:9).

Figure 3:
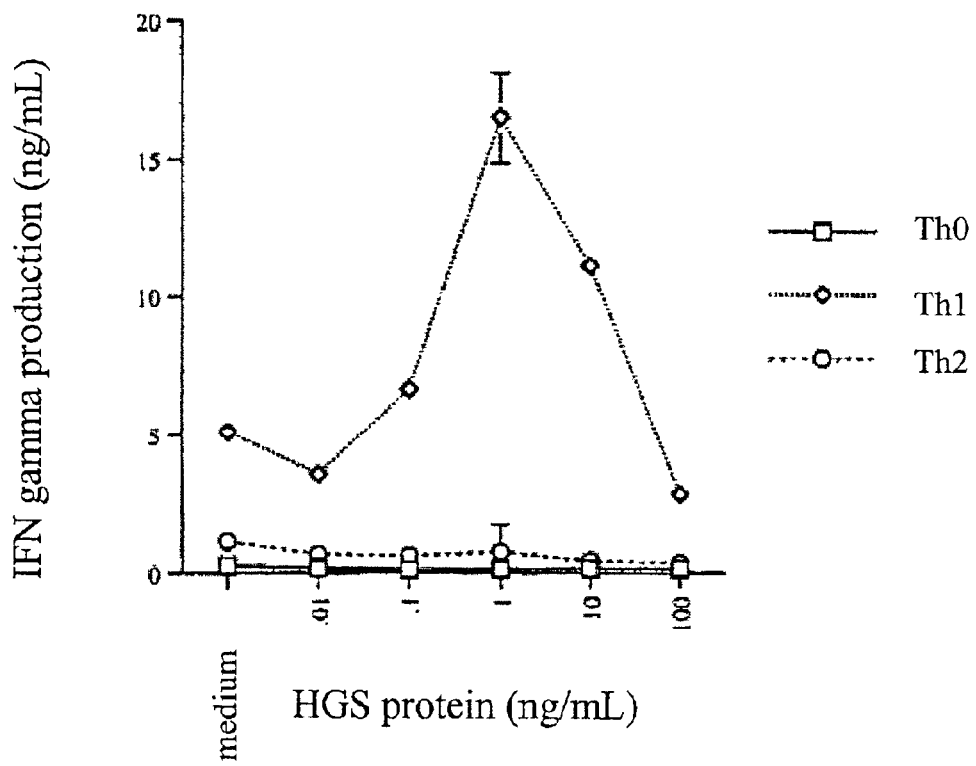
FIG. 3 is an illustration of the effect of HTTER36 on IFN gamma production by Th0, Th1 and Th2 cells.

In accordance with an aspect of the present invention, there is provided an isolated nucleic acid (polynucleotide) which encodes for the mature polypeptide having the deduced amino acid sequence of FIGS. 1A–B (SEQ ID NO:2).

The polynucleotide of this invention was discovered in a human testes tumor cDNA library. It is structurally related to the TGFβ gene super-family. It contains an open reading frame encoding a polypeptide of 364 amino acids, of which the first 16 amino acids are a putative leader sequence, the next 234 amino acids are a pro-sequence and the last 114 amino acids are the active region. HTTER36 exhibits the highest degree of homology at the amino acid level to GDF-3 with 69% identity and 80% similarity.

Expression of GDF-3 mRNA has been Observed in Human Kidney Tissue.

The first 16 amino acids represent a putative transmembrane portion which is thought to be necessary to direct the polypeptide to particular target locations for the carrying out of biological functions as hereinafter described. The transmembrane portion may also be cleaved from the polypeptide.

In accordance with another aspect of the present invention there are provided isolated polynucleotides encoding a mature polypeptide expressed by the human cDNA contained in ATCC Deposit No. 97349, deposited with the American Type Culture Collection, 10801 University Boulevard, Manassas, Va. 20110-2209, USA, on Nov. 29, 1995. The deposited material is a pBluescript SK(+) plasmid that contains the full-length HTTER36 cDNA, referred to as "PF230" when deposited.

The deposit has been made under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 35 U.S.C. § 112. The sequence of the polynucleotides contained in the deposited materials, as well as the amino acid sequence of the polypeptides encoded thereby, are controlling in the event of any conflict with any description of sequences herein. A license may be required to make, use or sell the deposited materials, and no such license is hereby granted References to "polynucleotides" throughout this specification includes the DNA of the deposit referred to above.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–B (SEQ ID NO:1) or may be a different coding sequence which coding sequence, as a result of the redundancy or degeneracy of the genetic code, encodes the same mature polypeptide as the DNA of FIGS. 1A–B (SEQ ID NO:1).

The polynucleotide which encodes for the mature polypeptide of FIGS. 1A–B (SEQ ID NO:2) may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide that includes only coding sequence for the polypeptide as well as a polynucleotide that includes additional coding and/or non-coding sequence.

The present invention further relates to variants of the hereinabove described polynucleotides which encode for fragments, analogs and derivatives of the polypeptide having the deduced amino acid sequence of FIGS. 1A–B (SEQ ID NO:2). The variant of the polynucleotide may be a naturally occurring allelic variant of the polynucleotide or a non-naturally occurring variant of the polynucleotide.

Particularly preferred variants include the following:

254–364
255–364
256–364
257–364
258–364
259–364
260–364
261–364

These variants would be expected to maintain GDF-3 activity because they all include the cystine at position 261, which is believed to be required for the structural integrity of GDF-3. Polynucleotides encoding such polypeptides are also provided.

Thus, the present invention includes polynucleotides encoding the same mature polypeptide as shown in FIGS. 1A–B (SEQ ID NO:2) as well as variants of such polynucleotides which variants encode for a fragment, derivative or analog of the polypeptide of FIGS. 1A–B (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–B (SEQ ID NO:1). As known in the art, an allelic variant is an alternate form of a polynucleotide sequence, which may have a substitution, deletion, or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence that allows for purification of the polypeptide of the present invention. The marker sequence may be a hexa-histidine tag supplied by a pQE vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length HTTER36 gene may be used as a hybridization probe for a cDNA library to isolate the full-length gene and to isolate other genes that have a high sequence similarity to the gene or similar biological activity. Probes of this type preferably have at least 15 bases, more preferably at least 30 bases and even more preferably may contain, for example, at least 50 or more bases. The probe may also be used to identify a cDNA clone corresponding to a full-length transcript and a genomic clone or clones that contain the complete HTTER36 gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides that hybridize to the hereinabove-described sequences if there is at least 70%, preferably at least 90%, and more preferably at least 95% identity between the sequences. The present invention particularly relates to polynucleotides that hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNA of FIGS. 1A–B (SEQ ID NO:1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 and polynucleotides complementary thereto as well as portions thereof, which portions have at least 15 consecutive or preferably at least 30 consecutive bases and most preferably at least 50 consecutive bases and to polypeptides encoded by such polynucleotides.

The present invention further relates to a polypeptide that has the deduced amino acid sequence of FIGS. 1A–B (SEQ ID NO:2), as well as fragments, analogs and derivatives of such polypeptide.

The terms "fragment," "derivative" and "analog" when referring to the polypeptide of FIGS. 1A–B (SEQ ID NO:2), means a polypeptide that retains essentially the same biological function or activity as such polypeptide. Thus, an analog includes a proprotein that can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–B (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors that include polynucleotides of the present invention, host cells which are genetically engineered with vectors of the invention and the production of polypeptides of the invention by recombinant techniques.

Host cells are genetically engineered (transduced or transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: PWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics for human disease.

The specificity of HTTER36 for target cells can be exploited as a mechanism to destroy the target cell. For example, HTTER36 or soluble forms thereof can be coupled (by a wide variety of methods) to toxic molecules: for example, a radiopharmaceutical that inactivates target cells. These growth factor-toxin fusions kill the target cell (ard in certain cases neighboring cells by a variety of "bystander" effects). A recent example of such toxin-fusion genes is published by Mesri, et al., J. Biol. Chem. 268:4853–62 (1993). HTTER36 and soluble fragments thereof and related molecules may also be encapsulated in liposomes and may be conjugated to antibodies which recognize and bind to tumor or cell specific antigens, thereby provided a means for "targeting" cells.

In this same manner, HTTER36 and soluble fragments thereof can be employed as an anti-neoplastic compound, since members of this family show anti-proliferative effects on transformed cells. For in vivo use, the subject polypeptide may be administered in a variety of ways, including but not limited to, injection, infusion, topically, parenterally, etc. Administration may be in any physiologically acceptable carrier, including phosphate buffered saline, saline, sterilized water, etc.

A significant treatment involving HTTER36 and soluble fragments thereof relates to wound healing. The compositions of the present invention may be employed for treating a wide variety of wounds including substantially all cutaneous wounds, corneal wounds, and injuries to the epithelial-lined hollow organs of the body. Wounds suitable for treatment include those resulting from trauma such as burns, abrasions and cuts, as well as from surgical procedures such as surgical incisions and skin grafting. Other conditions suitable for treatment with the polypeptide of the present invention include chronic conditions, such as chronic ulcers, diabetic ulcers, and other non-healing (trophic) conditions.

HTTER36 and soluble fragments thereof may be incorporated in physiologically-acceptable carriers for application to the affected area. The nature of the carriers may vary widely and will depend on the intended location of application. For application to the skin, a cream or ointment base is usually preferred; suitable bases include lanolin, Silvadene (Marion) (particularly for the treatment of burns), Aquaphor (Duke Laboratories, South Norwalk, Conn.), and the like. If desired, it will be possible to incorporate HTTER36 containing compositions in bandages and other wound dressings to provide for continuous exposure of the wound to the peptide. Aerosol applications may also find use.

The concentration of HTTER36 in the treatment composition is not critical but should be enough to induce epithelial cell proliferation. The compositions may be applied topically to the affected area, typically as eye drops to the eye or as creams, ointments or lotions to the skin. In the case of the eyes, frequent treatment is desirable, usually being applied at intervals of 4 hours or less. On the skin, it is desirable to continually maintain the treatment composition on the affected area during the healing, with applications of the treatment composition from two to four times a day or more frequently.

The amount employed of the subject polypeptide will vary with the manner of administration, the employment of other active compounds, and the like, generally being in the range of about 1 $\mu$g to 100 $\mu$g. The subject polypeptide may be employed with a physiologically acceptable carrier, such as saline, phosphate-buffered saline, or the like. The amount of compound employed will be determined empirically, based on the response of cells in vitro and response of experimental animals to the subject polypeptides or formulations containing the subject polypeptides.

HTTER36 and soluble fragments thereof may be employed to stimulate the anchorage-independent growth of normal rat kidney fibroblasts.

HTTER36 and soluble fragments thereof may be employed as a multi-functional regulator of cell growth and differentiation being capable of such diverse effects of inhibiting the growth of several human cancer cell lines, and T and B lymphocytes.

HTTER36 and soluble fragments thereof may also be employed to inhibit early hematopoietic progenitor cell proliferation, stimulates the induction of differentiation of rat muscle mesenchymal cells and stimulate production of cartilage-specific macro molecules, causing increased synthesis and secretion of collagen.

HTTER36 and soluble fragments thereof may also be employed to stimulate bone formation.

This invention provides a method of screening compounds to identify antagonist compounds to the polypeptide of the present invention. As an example, a mammalian cell or membrane preparation expressing a HTTER36 receptor is incubated with a potential compound and the ability of the compound to generate a second signal from the receptor is measured to determine if it is an effective antagonist. Such second messenger systems include but are not limited to, cAMP guanylate cyclase, ion channels or phosphoinositide hydrolysis. Effective antagonists are also determined by the method above wherein an antagonist compound is detected which binds to the receptor but does not elicit a second messenger response to thereby block the receptor from HTTER36.

The inventors have determined according to Example 5, that HTTER36 may be used to enhance the differentiation of T helper cells in functional T helper 1 cells. Thus, it is believed that HTTER36 may be used as a therapeutic to enhance the cellular immune response.

Accordingly, it is believed the HTTER36 polypeptides may be used to treat inflammatory diseases such as, Lyme's disease, arthritis, reactive arthritis, contact dermatitis as well as malaria-induced vascular disease. HTTER36 may also be useful in the treatment of autoimmune diseases such as multiple sclerosis and Crohn's disease. HTTER36 may also be useful in the treatment of infectious diseases such as AIDS, candidiasis, *listeria* and *toxoplasma*.

Another assay for identifying potential antagonists specific to the receptors to the polypeptide of the present invention is a competition assay, which comprises isolating plasma membranes that over-express a receptor to the polypeptide of the present invention, for example, human A431 carcinoma cells. Serially diluted test sample in a medium (volume is approximately 10 microliters) containing 10 nM $^{125}$I-HTTER36 is added to five micrograms of the plasma membrane in the presence of the potential antagonist compound and incubated for 4 hours at 4° C. The reaction mixtures are diluted and immediately passed through a millipore filter. The filters are then rapidly washed and the bound radioactivity is measured in a gamma counter. The amount of bound HTTER36 is then measured. A control assay is also performed in the absence of the compound to determine if the antagonists reduce the amount of bound HTTER36.

Potential antagonist compounds include an antibody, or in some cases, an oligopeptide, which binds to the polypeptide. Alternatively, a potential antagonist may be a closely related protein that binds to the receptor, which is an inactive form of the polypeptide, and thereby prevent the action of the polypeptide of the present invention.

Another antagonist compound is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the polypeptide of the present invention. The antisense RNA oligonucleotide hybridizes to the mRNA in vivo and blocks translation of the mRNA molecule into the polypeptide of the present invention (Antisense-Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptide of the present invention.

Antagonist compounds include a small molecule that binds to the polypeptide of the present invention and blocks its action at the receptor such that normal biological activity is prevented. The small molecules may also bind the receptor to the polypeptide to prevent binding. Examples of small molecules include but are not limited to small peptides or peptide-like molecules.

The antagonists may be employed to treat neoplasia, for example, cancers and tumors, in cells whose growth are stimulated by the polypeptide of the present invention.

The antagonists may also be employed to prevent the stimulation of formation of extracellular matrix molecules in the liver and lung.

The polypeptides of the present invention or antagonist compounds may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or compounds of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount that is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The polypeptides, and antagonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter, and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters that may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter, inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter, retroviral LTRs (including the modified retroviral LTRs hereinabove described); the β-actin promoter; and human growth hormone promoters. The promoter also may be the native promoter that controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles that include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells that may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene of the present invention will allow a diagnosis of a disease or a susceptibility to a disease which results from under expression of the polypeptide of the present invention, for example, improper wound healing and improper neurological functioning.

Individuals carrying mutations in the human gene of the present invention may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding a polypeptide of the present invention can be used to identify and analyze mutations thereof. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobility of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to diagnostic assays for detecting altered levels of the polypeptide of the present invention in various tissues since an over-expression of the proteins compared to normal control tissue samples can detect the presence of certain disease conditions such as neoplasia, skin disorders, ocular disorders and inflammation. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to an antigen of the polypeptide of the present invention, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, which binds the proteins in the sample. Any free protein binding sites on the dish are then covered by incubating with a non-specific protein such as bovine serum albumin. Next, the monoclonal antibody is incubated in the dish during which time the monoclonal antibodies attach to any polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to polypeptides of the present invention. Unattached reporter antibody is then washed out. Peroxidase substrates are then added to the dish and the amount of color developed in a given time period is a measurement of the amount of protein present in a given volume of patient sample when compared against a standard curve.

A competition assay may also be employed to determine levels of the polypeptide of the present invention in a sample derived from the hosts. Such an assay comprises isolating plasma membranes that over-express the receptor for the polypeptide of the present invention. A test sample containing the polypeptides of the present invention that have been labeled, are then added to the plasma membranes and then incubated for a set period of time. Also added to the reaction mixture is a sample derived from a host that is suspected of containing the polypeptide of the present invention. The reaction mixtures are then passed through a filter that is rapidly washed and the bound radioactivity is then measured to determine the amount of competition for the receptors and therefore the amount of the polypeptides of the present invention in the sample.

Antibodies specific to HTTER36 may be used for cancer diagnosis and therapy, since many types of cancer cells up-regulate various members of this super family during the process of neoplasia or hyperplasia. These antibodies bind to and inactivate HTTER36. Monoclonal antibodies against HTTER36 (and/or its family members) are in clinical use for both the diagnosis and therapy of certain disorders including (but not limited to) hyperplastic and neoplastic growth abnormalities. Up-regulation of growth factor expression by neoplastic tissues forms the basis for a variety of serum assays that detect increases in growth factor in the blood of affected patients. These assays are typically applied not only in diagnostic settings, but are applied in prognostic settings as well (to detect the presence of occult tumor cells following surgery, chemotherapy, etc).

In addition, malignant cells expressing the HTTER36 receptor may be detected by using labeled HTTER36 in a receptor binding assay, or by the use of antibodies to the HTTER36 receptor itself. Cells may be distinguished in accordance with the presence and density of receptors for HTTER36, thereby providing a means for predicting the susceptibility of such cells to the biological activities of HTTER36.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosore. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique that provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands that may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

Example 1

Bacterial Expression and Purification of Mature HTTER36

The DNA sequence encoding HTTER36, ATCC #97349, was initially amplified using PCR oligonucleotide primers corresponding to the 5' sequences of the processed HTTER36 protein and the vector sequences 3' to the HTTER36 gene. Additional nucleotides corresponding to HTTER36 were added to the 5' and 3' sequences respectively. The 5' oligonucleotide primer has the sequence 5' GAAAGGATCCGCAGCCATCCCTGTC-CCCAAACTTTCTTGT 3' (SEQ BD NO:3) contains a BamHI restriction enzyme site (in bold) followed by 18 nucleotides of HTTER36 coding sequence starting from nucleotide 791 of FIGS. 1A–B (SEQ ID NO:1). The 3' sequence 5' TCCTTCTATTCAAGCTTCTGACATC-CTACCCACACCCACA 3' (SEQ ID NO:4) contains complementary sequences to a Hind III site and is followed by 15 nucleotides of HTTER36 beginning at nucleotide 1121, and a stop codon. The restriction enzyme sites correspond to the restriction enzyme sites on the bacterial expression vector pQE-9 (Qiagen, Inc. Chatsworth, Calif., 91311). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 was then digested with BamHI and Hind III.

The amplified sequences were ligated into pQE-9 and were inserted in frame with the sequence encoding for the histidine tag and the RBS. The ligation mixture was then used to transform E. coli strain DH5 alpha (Gibco BRL) the procedure described in Sambrook, J. et al., Molecular Cloning: A Laboratory Manual, Cold Spring Laboratory Press, (1989). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl.

After clarification, solubilized HTTER36 was purified from this solution by chromatography on a Nickel-Chelate column under conditions that allow for tight binding by proteins containing the 6-His tag (Hochuli, E. et al., J. Chromatography 411:177–184 (1984)). HTTER36 (85% pure) was eluted from the column in 6 molar guanidine HCl pH 5.0 and for the purpose of renaturation adjusted to 3 molar guanidine HCl, 100 mM sodium phosphate, 10 molar glutathione (reduced) and 2 molar glutathione (oxidized). After incubation in this solution for 12 hours the protein was dialyzed to 10 molar sodium phosphate.

Example 2

Cloning and Expression HTTER36 using the Baculovirus Expression System

The DNA sequence encoding the HTTER36 protein, ATCC # 97349, is amplified using PCR oligonucleotide primers corresponding to the 5' and 3' sequences of the gene.

The primers used are: 5' CAGGGATCCGCCATCAT-GCTTCGTTTCTTGCCAGA 3' (SEQ ID NO:5) contains the underlined Bam HI site an efficient signal for the initiation of translation in eukaryotic cells, a start codon (bold) and 17 bps of HTTER36 coding sequence. The 3' primer has the sequence 5' CTTCGGTACCCATTTCTGA-CATCCTACCCACAC 3' (SEQ 1) NO:6) contains the underlined Asp718 site, and 23 nucleotides complementary to the 3' end of the HTTER36 sequence beginning at nucleotide 1126.

The amplified sequences are isolated from a 1% agarose gel using a commercially available kit ("Geneclean," BIO 101 Inc., La Jolla, Calif.). The fragment is then digested with the endonucleases BamHI and Asp718 and then purified again on a 1% agarose gel. This fragment is designated F2.

The vector pA2 is used (modification of pVL941 vector, discussed below) for the expression of the HTTER36 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used such as pAc373, pRG1, pVL941 and pAcIM1 (Luckow, V. A. and Summers, M. D., Virology, 170:31–39).

The plasmid is digested with the restriction enzymes BamHI and Asp718 and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. E. coli HB101 cells are then transformed and bacteria identified that contained the plasmid (pBacHTTER36) with the HTTER36 gene using the restriction enzymes BamHI and Asp718. The sequence of the cloned fragment is confirmed by DNA sequencing.

5 µg of the plasmid pBacHTTER36 is co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacHTTER36 are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-HTTER36 at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours before they are harvested by centrifugation and the labeled proteins visualized by SDS-PAGE and autoradiography.

Example 3

Expression of Recombinant HTTER36 in CHO Cells

The vector pC1 is used for the expression of the HTTER36 protein. Plasmid pC1 is a derivative of the plasmid pSV2-dhfr [ATCC Accession No. 37146]. Both plasmids contain the mouse dhfr gene under control of the SV40 early promoter. Chinese hamster ovary- or other cells lacking dihydrofolate activity that are transfected with these plasmids can be selected by growing the cells in a selective medium (alpha minus MEM, Lift Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the dhfr gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pN346 contains for the expression of the gene of interest a strong promoter of the long terminal repeat (LTR) of the Rouse Sarcoma Virus (Cullen, et al., Molecular and Cellular Biology, March 1985, 438–447) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g. G418 plus methotrexate.

The plasmid pN346 was digested with the restriction enzyme BamHI and then dephosphorylated using calf intestinal phosphatase by procedures known in the art. The vector was then isolated from a 1% agarose gel.

The DNA sequence encoding HTTER36, ATCC# 97349 was amplified using PCR oligonucleotide primers corresponding to the 5' and 3' sequences of the gene:

The 5' primer has the sequence 5' ACAGCGGATC-CAGCCACC ATGCTTCGTTTCTTGCCA 3' (SEQ ID NO:7) and contains a BamHI restriction enzyme site (in bold) followed by an efficient signal for translation (Kozak, M., supra) plus the first 18 nucleotides of the gene (the initiation codon for translation "ATG" is underlined).

The 3' primer has the sequence 5' TCCTTCGGATC-CCATTTCT GACATCCTACCCACACCCACA 3' (SEQ ID NO:8) and contains the cleavage site for the restriction endonuclease BamHI and 29 nucleotides complementary to the 3' translated and non-translated sequence of the gene.

The amplified fragments were isolated from a 1% agarose gel as described above and then digested with the endonuclease BglII and then purified again on a 1% agarose gel.

The isolated fragment and the dephosphorylated vector were then ligated with T4 DNA ligase. *E. coli* HB101 cells were then transformed and bacteria identified that contained the plasmid pN346 inserted in the correct orientation using the restriction enzyme BamHI. The sequence of the inserted gene was confirmed by DNA sequencing.

Transfection of CHO-dhfr-Cells

Chinese hamster ovary cells lacking an active DHFR enzyme were used for transfection. 5 μg of the expression plasmid N346 were cotransfected with 0.5 μg of the plasmid pSVneo using the lipofectin method (Felgner et al., supra). The plasmid pSV2-neo contains a dominant selectable marker, the gene neo from Tn5 encoding an enzyme that confers resistance to a group of antibiotics including G418. The cells were seeded in alpha minus MEM supplemented with 1 mg/ml G418. After 2 days, the cells were trypsinized and seeded in hybridoma cloning plates (Greiner, Germany) and cultivated from 10–14 days. After this period, single clones were trypsinized and then seeded in 6-well petri dishes using different concentrations of methotrexate (25, 50 nm, 100 nm, 200 nm, 400 nm). Clones growing at the highest concentrations of methotrexate were then transferred to new 6-well plates containing even higher concentrations of methotrexate (500 nM, 1 μM, 2 μM, 5 μM). The same procedure was repeated until clones grew at a concentration of 100 μM.

The expression of the desired gene product was analyzed by Western blot analysis and SDS-PAGE.

Example 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers that correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB 101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 5

Effects of HTTER36 on Th1/Th2 Differentiation

To determine the effect of HTTER36 on human Th1/Th2 differentiation an assay where naive human DCD4+ T cells are induced to differentiate under neutral (Th0), Th1 or Th2 conditions was used. Naive CD4, CD45RA T cells are purified from human cord blood (Poietic Technologies, Germantown, Md.) and cultured (0.75×10 6 cells/750 μl) in 24 well plates in RPMI-1640-10% FCS in the presence of the T cell mitogen PHA (1 ug/ml) under the following conditions:

Neutral: medium containing isotype matched control mAB (murine IgG1 from Cappell)

Th1 directed: in the presence of IL-12 (0.1 ng/ml) and anti-IL-4 (mAB 5A4 ascites 1:200)

Th2 directed; in the presence of IL-4 (0.1 ng/ml) and anti-IL-12 (mAb C.8.6, 1 ug/ml).

HTTER36 and positive controls (IL-12, 5 ng/ml for Th1 and IL-4, 5 ng/ml for Th2) are added at the initiation of culture. After 5 days of culture at 37C the plates are spun down and the supernatants removed. The cells are then restimulated with fresh medium containing stimulatory anti-CD3 (HIT3a 1 μg/ml) and IL-2 (10 U/ml) HTTER36 or positive/negative controls, but omitting the directing cytokines and antibodies. After an additional 48 hours of culture at 37° C. the plates are spun down and supernatants measured for IFN-γ (Th1) and IL-4 (Th2) by ELISA.

The results are shown in FIG. 3. In this experiment, the positive control (IL-12) induced IFN-γ production under neutral, Th1 conditions and Th2 conditions. In this experiment culture medium alone, under Th1 directed conditions also resulted in significant IFNγ production. IL-4 also induced high levels of IFNγ under Th1 conditions. HTTER36 also induced IFNγ production above that observed with culture medium alone, but only under Th1 directed conditions with an optimal response at 1 ng/ml. This effect cannot be attributed to endotoxin, a potent inducer of IL-12, because it was not observed under Th0 conditions. No effect on IL-4 production has been observed with HTTER36.

Numerous modifications and variations of the present invention are possible in light of the above teachings andtherefore, within the scope of the appended claims, the invention may be practiced otherwise than as particularly described.

What is claimed is:

1. An isolated antibody or fragment thereof that specifically binds to a protein selected from the group consisting of:
   (a) a protein consisting of amino acid residues 1 to 364 of SEQ ID NO:2;
   (b) a protein consisting of amino acid residues 17 to 364 of SEQ ID NO:2;
   (c) a protein consisting of amino acid residues 251 to 364 of SEQ ID NO:2; and
   (d) a protein consisting of a portion of SEQ ID NO:2, wherein said portion is at least 50 contiguous amino acid residues in length,
   wherein said antibody or fragment thereof does not bind mouse GDF3 (SEQ ID NO:9).

2. The antibody or fragment thereof of claim 1 that specifically binds protein (a).

3. The antibody or fragment thereof of claim 2 that specifically binds protein (b).

4. The antibody or fragment thereof of claim 1 that specifically binds protein (b).

5. The antibody or fragment thereof of claim 1 that specifically binds protein (c).

6. The antibody or fragment thereof of claim 5 wherein said protein bound by said antibody or fragment thereof is glycosylated.

7. The antibody or fragment thereof of claim 5 which is polyclonal.

8. The antibody or fragment thereof of claim 5 which is selected from the group consisting of:
   (a) a single chain antibody; and
   (b) a Fab fragment.

9. The antibody or fragment thereof of claim 5 wherein said antibody or fragment thereof specifically binds to said protein in a Western blot.

10. The antibody or fragment thereof of claim 5 wherein said antibody or fragment thereof specifically binds to said protein in an ELISA.

11. An isolated cell that produces the antibody or fragment thereof of claim 5.

12. A hybridoma that produces the antibody or fragment thereof of claim 5.

13. A method of detecting a protein in a biological sample comprising:
   (a) contacting the biological sample with the antibody or fragment thereof of claim 5; and
   (b) detecting the protein in the biological sample.

14. The method of claim 13 wherein the antibody or fragment thereof is polyclonal.

15. The antibody or fragment thereof of claim 5 which is chimeric.

16. The antibody or fragment thereof of claim 1 that specifically binds protein (d).

17. An isolated antibody or fragment thereof obtained from an animal that has been immunized with a protein selected from the group consisting of:
   (a) a protein consisting of amino acid residues 1 to 364 of SEQ ID NO:2;
   (b) a protein consisting of amino acid residues 17 to 364 of SEQ ID NO:2;
   (c) a protein consisting of amino acid residues 251 to 364 of SEQ ID NO:2; and
   (d) a protein consisting of a portion of SEQ ID NO:2, wherein said portion is at least 50 contiguous amino acid residues in length, wherein said antibody or fragment thereof specifically binds to said amino acid residues and wherein said antibody or fragment thereof does not bind to mouse GDF3 (SEQ ID NO:9).

18. The antibody or fragment thereof of claim 17 obtained from an animal immunized with protein (a).

19. The antibody or fragment thereof of claim 17 obtained from an animal immunized with protein (b).

20. The antibody or fragment thereof of claim 17 obtained from an animal immunized with protein (c).

21. The antibody or fragment thereof of claim 17 obtained from an animal immunized with protein (d).

22. The antibody or fragment thereof of claim 17 which is monoclonal.

23. The antibody or fragment thereof of claim 17 which is selected from the group consisting of:
   (a) a single chain antibody; and
   (b) a Fab fragment.

24. The antibody or fragment thereof of claim 17 which is chimeric.

25. The antibody or fragment thereof of claim 17 which is polyclonal.

26. An isolated monoclonal antibody or fragment thereof that specifically binds to a protein selected from the group consisting of:
   (a) a protein consisting of amino acid residues 1 to 364 of SEQ ID NO:2;
   (b) a protein consisting of amino acid residues 17 to 364 of SEQ ID NO:2;
   (c) a protein consisting of amino acid residues 251 to 364 of SEQ ID NO:2; and
   (d) a protein consisting of a portion of SEQ ID NO:2, wherein said portion is at least 50 contiguous amino acid residues in length,
   wherein said antibody or fragment thereof does not bind to mouse GDF3 (SEQ ID NO:9).

27. The antibody or fragment thereof of claim 26 that specifically binds protein (a).

28. The antibody or fragment thereof of claim 27 that specifically binds protein (b).

29. The antibody or fragment thereof of claim 26 that specifically binds protein (b).

30. The antibody or fragment thereof of claim 26 that specifically binds protein (c).

31. The antibody or fragment thereof of claim 30 wherein said protein bound by said antibody or fragment thereof is glycosylated.

32. The antibody or fragment thereof of claim 30 which is selected from the group consisting of:
   (a) a single chain antibody; and
   (b) a Fab fragment.

33. The antibody or fragment thereof of claim 30 wherein said antibody or fragment thereof specifically binds to said protein in a Western blot.

34. The antibody or fragment thereof of claim 30 wherein said antibody or fragment thereof specifically binds to said protein in an ELISA.

35. An isolated cell that produces the antibody or fragment thereof of claim 30.

36. A hybridoma that produces the antibody or fragment thereof of claim 30.

37. A method of detecting a protein in a biological sample comprising:
   (a) contacting the biological sample with the antibody or fragment thereof of claim 30; and
   (b) detecting the protein in the biological sample.

38. The antibody or fragment thereof of claim 30 which is chimeric.

39. The antibody or fragment thereof of claim 26 that specifically binds protein (d).

40. An isolated antibody or fragment thereof that specifically binds to a protein consisting of the full-length polypeptide encoded by the cDNA contained in ATCC Deposit Number 97349, wherein said antibody or fragment thereof does not bind to mouse GDF3 (SEQ ID NO:9).

41. The antibody or fragment thereof of claim 40 wherein said protein bound by said antibody or fragment thereof is glycosylated.

42. The antibody or fragment thereof of claim 40 which is polyclonal.

43. The antibody or fragment thereof of claim 40 which is selected from the group consisting of:
   (a) a single chain antibody; and
   (b) a Fab fragment.

44. The antibody or fragment thereof of claim 40 wherein said antibody or fragment thereof specifically binds to said protein in a Western blot.

45. The antibody or fragment thereof of claim 40 wherein said antibody or fragment thereof specifically binds to said protein in an ELISA.

46. An isolated cell that produces the antibody or fragment thereof of claim 40.

47. A hybridoma that produces the antibody or fragment thereof of claim 40.

48. A method of detecting a protein in a biological sample comprising:
   (a) contacting the biological sample with the antibody or fragment thereof of claim 40; and
   (b) detecting the protein in the biological sample.

49. The method of claim 48 wherein the antibody or fragment thereof is a polyclonal antibody.

50. The antibody or fragment thereof of claim 40 which is chimeric.

51. An isolated antibody or fragment thereof obtained from an animal that has been immunized with a protein comprising the amino acid sequence of the full-length polypeptide encoded by the cDNA contained in ATCC Deposit Number 97349, wherein said antibody or fragment thereof specifically binds to said amino acid sequence, and wherein said antibody or fragment thereof does not bind to mouse GDF3 (SEQ ID NO:9).

52. The antibody or fragment thereof of claim 51 which is monoclonal.

53. The antibody or fragment thereof of claim 51 which is selected from the group consisting of:
   (a) a single chain antibody; and
   (b) a Fab fragment.

54. The antibody or fragment thereof of claim 51 which is chimeric.

55. The antibody or fragment thereof of claim 51 which is polyclonal.

56. An isolated monoclonal antibody or fragment thereof that specifically binds to a protein consisting of the full-length polypeptide encoded by the cDNA contained in ATCC Deposit Number 97349, wherein said antibody or fragment thereof does not bind to mouse GDF3 (SEQ ID NO:9).

57. The antibody or fragment thereof of claim 56 wherein said protein bound by said antibody or fragment thereof is glycosylated.

58. The antibody or fragment thereof of claim 56 which is selected from the group consisting of:
(a) a single chain antibody; and
(c) a Fab fragment.

59. The antibody or fragment thereof of claim 56 wherein said antibody or fragment thereof specifically binds to said protein in a Western blot.

60. The antibody or fragment thereof of claim 56 wherein said antibody or fragment thereof specifically binds to said protein in an ELISA.

61. An isolated cell that produces the antibody or fragment thereof of claim 56.

62. A hybridoma that produces the antibody or fragment thereof of claim 56.

63. A method of detecting a protein in a biological sample comprising:
(a) contacting the biological sample with the antibody or fragment thereof of claim 56; and
(b) detecting the protein in the biological sample.

64. The antibody or fragment thereof of claim 56 which is chimeric.

65. An isolated antibody or fragment thereof that specifically binds a protein purified from a cell culture wherein said protein is encoded by a polynucleotide encoding amino acids 17 to 364 of SEQ ID NO:2, and wherein said antibody or fragment thereof does not bind to mouse GDF3 (SEQ ID NO:9).

66. The antibody or fragment thereof of claim 65 which is monoclonal.

67. The antibody or fragment thereof of claim 65 which is selected from the group consisting of:
(a) a single chain antibody; and
(b) a Fab fragment.

68. The antibody or fragment thereof of claim 65 wherein said antibody or fragment thereof specifically binds to said protein in a Western blot.

69. The antibody or fragment thereof of claim 65 wherein said antibody or fragment thereof specifically binds to said protein in an ELISA.

70. The antibody or fragment thereof of claim 65 which is chimeric.

71. The antibody or fragment thereof of claim 65 which is polyclonal.

* * * * *